(12) United States Patent
Forsgren Brusk et al.

(10) Patent No.: US 8,222,020 B2
(45) Date of Patent: Jul. 17, 2012

(54) **BIOLOGICALLY PURE STRAIN OF *LACTOBACILLUS FERMENTUM*, STRAIN ESS-1**

(75) Inventors: Ulla Forsgren Brusk, Pixbo (SE); Ulrika Husmark, Mölnlycke (SE); Eva Grahn Håkansson, Umeå (SE); Daniel Rönnqvist, Umeå (SE)

(73) Assignee: SCA Hygiene Products AB, Gothenburg (SE)

( * ) Notice: Subject to any disclaimer, the term of this patent is extended or adjusted under 35 U.S.C. 154(b) by 247 days.

(21) Appl. No.: 12/515,252

(22) PCT Filed: Nov. 17, 2006

(86) PCT No.: PCT/SE2006/001311
§ 371 (c)(1), (2), (4) Date: May 15, 2009

(87) PCT Pub. No.: WO2008/060198
PCT Pub. Date: May 22, 2008

(65) Prior Publication Data
US 2010/0069860 A1 Mar. 18, 2010

(51) Int. Cl.
*C12N 1/20* (2006.01)
(52) U.S. Cl. .................. 435/252.9; 424/93.45
(58) Field of Classification Search .................. None
See application file for complete search history.

(56) References Cited

U.S. PATENT DOCUMENTS

| | | | |
|---|---|---|---|
| 6,110,908 A | 8/2000 | Guthery | |
| 6,531,126 B2 | 3/2003 | Farmer | |
| 6,716,435 B1 | 4/2004 | Farmer et al. | |
| 6,761,885 B1 | 7/2004 | Hakansson et al. | |
| 7,482,023 B2 | 1/2009 | Runeman et al. | |
| 2001/0033838 A1 | 10/2001 | Farmer | |
| 2002/0044926 A1* | 4/2002 | Reid et al. | 424/93.45 |
| 2002/0090365 A1 | 7/2002 | Chrisope | |
| 2003/0143262 A1 | 7/2003 | Brusk et al. | |
| 2004/0142832 A1 | 7/2004 | Runeman et al. | |
| 2004/0241151 A1 | 12/2004 | Husmark et al. | |
| 2004/0243076 A1 | 12/2004 | Husmark et al. | |
| 2004/0253217 A1* | 12/2004 | Samuelsson et al. | 424/93.45 |
| 2005/0276836 A1 | 12/2005 | Wilson et al. | |
| 2006/0171936 A1 | 8/2006 | Gueniche et al. | |
| 2006/0177429 A1 | 8/2006 | Farmer et al. | |
| 2010/0030172 A1 | 2/2010 | Husmark et al. | |
| 2010/0040673 A1 | 2/2010 | Husmark et al. | |
| 2010/0136210 A1 | 6/2010 | Forsgren-Brusk et al. | |

FOREIGN PATENT DOCUMENTS

| | | |
|---|---|---|
| EP | 1 060 240 B1 | 12/2001 |
| EP | 1 140 226 | 3/2006 |
| RU | 2212902 (C2) | 9/2003 |
| WO | WO 92/13577 | 8/1992 |
| WO | WO 94/23585 | 10/1994 |
| WO | WO 97/02846 A1 | 1/1997 |
| WO | WO 98/46261 | 10/1998 |
| WO | WO 99/17788 | 4/1999 |
| WO | WO 99/17813 A1 | 4/1999 |
| WO | WO 99/45099 A1 | 9/1999 |
| WO | WO 99/45976 | 9/1999 |
| WO | WO 00/35502 A1 | 6/2000 |
| WO | WO 00/61201 | 10/2000 |
| WO | WO 00/76878 | 12/2000 |
| WO | WO 02/28446 | 4/2002 |
| WO | WO 03/038068 A1 | 5/2003 |
| WO | WO 2004/022727 A1 | 3/2004 |
| WO | WO 2004/060416 A1 | 7/2004 |
| WO | WO 2005/086870 | 9/2005 |
| WO | WO 2008/060199 | 5/2008 |
| WO | WO 2008/060200 | 5/2008 |

OTHER PUBLICATIONS

L. Beuchat, "Comparison of Anti-*Vibro* Activities of Potassium Sorbate, Sodium Benzoate, and Glycerol and Sucros Esters of Fatty Acids," Applied and Environmental Microbiology, Jun. 1980, pp. 1178-1182, vol. 39, No. 6.
PCT/ISA/210 mailed Jul. 6, 2007.
PCT/ISA/237 mailed Jul. 6, 2007.
V Redondo-Lopez, "Emerging Role of Lactobacilli in the Control and Maintenance of the Vaginal Bacterial Microflora" Sep.-Oct. 1990, pp. 856-872, vol. 12 No. 5.
T Hooton "*Escherichia coli* Bacteriuria and Contraceptive Method" JAMA, Jan. 2, 1991, vol. 265, No. 1.
F Rainey "The Genus Nocardiopsis Represents a Phylogenetically Coherent Taxon and a Distinct Actinomycete Lineage: Proposal of Nocardiopsaceae fam. nov." International Journal of Systematic Bacteriology, Oct. 1996, pp. 1088-1092, vol. 46, No. 4.
M Falagas "Probiotics for prevention of recurrent vulvovaginal candidiasis: a review" Journal of Antimicrobial Chemotherapy Jun. 21, 2006, 58, 266-272.
M Strus "Dzialanie In Vitro Bakterii Z Rodzaju *Lactobacillus* Izolowanych Z Pochwy Na Grzybywywolujace Kandydoze Seomu I Pochwy"; Medcycyna doswiadczalna I mikrobiologia 2005, pp. 7-17, vol. 57, No. 1 in Russian with English Abstract.
D Ronnqvist "Inhibition of *Candida albicans* and *Candidia glabrata* by two *Lactobacillus fermentum* strains" Essum AB, Jun. 2008 pp. 11.
J Osset "Papel de *Lactobacillus* como factor protector de la candidiasis vaginal" Oct. 19, 2007pp. 285-289 in Spanish with English Abatract.
G B Hill "Bacteriology of the Vagina" pp. 23-29 Seattle, USA.

(Continued)

*Primary Examiner* — Irene Marx
(74) *Attorney, Agent, or Firm* — Buchanan Ingersoll & Rooney PC (57) ABSTRACT

A novel strain of *Lactobacillus fermentum*, denoted strain Ess-1, which has been deposited at Deutsche Sammlung von Mikroorganismen und Zellkulturen GmbH and has been assigned accession number DSM17851. *Lactobacillus fermentum*, strain Ess-1, has shown valuable properties in the inhibition of *Candida*, and has medical uses, in particular for the treatment and/or prevention of candidasis and urinary tract infections. In addition, pharmaceutical products and articles include the novel bacterial strain.

21 Claims, 4 Drawing Sheets

OTHER PUBLICATIONS

Russian Federation Office Action dated Apr. 27, 2010 in foreign Application No. 2009122992/15(031913); and translation thereof.

Rönnqvist et al., "*Lactobacillus fermantum* Ess-1 with unique Growth Inhibition of Vulvo-Vaginal Candidiasis Pathogens" Journal of Medical Microbiology, 2007, vol. 56, No. 11, pp. 1500-1504, XP002597677.

Rönnqvist et al., "Selection and Characterization of a *Lactobacillus plantarum* Strain Promising as a Urogenital Probiotic" Microbial Ecology in Health and Disease, 2005, vol. 17, No. 2, pp. 75-82, XP008125895.

Supplementary European Search Report dated Sep. 6, 2010, issued in the corresponding European Application No. 06813030.1-1212.

Maidak et al., "A New Version of the RDP (Ribosomal Database Project)" Nucleic Acids Research, 1999, vol. 27, No. 1, pp. 171-173.

Runeman et al., "Experimental *Candida albicans* Lesions in Healthy Humans: Dependence on Skin pH" Acta Derm Venereol, 2000, vol. 80, pp. 421-424.

International Search Report and the Written Opinion of the International Searching Authority Forms (PCT/ISA/210 and PCT/ISA/237) issued in corresponding International Application No. PCT/SE2006/001312 dated Jul. 5, 2007.

Written Opinion of the International Preliminary Examining Authority Form (PCT/IPEA/408) issued in corresponding International Application No. PCT/SE2006/001312 dated Jan. 27, 2009.

International Search Report and the Written Opinion of the International Searching Authority Forms (PCT/ISA/210 and PCT/ISA/237) issued in corresponding International Application No. PCT/SE2006/001313 dated Jun. 29, 2007.

Written Opinion of the International Preliminary Examining Authority Form (PCT/IPEA/408) issued in corresponding International Application No. PCT/SE2006/001313 dated Jan. 27, 2009.

Notification of Receipt of Record Copy Form (PCT/IB/301) issued in corresponding International Application No. PCT/SE2006/001313 dated Jan. 4, 2007.

Husmark et al., U.S. Appl. No. 12/514,909, entitled "Sanitary Article Comprising a Microbe-Inhibiting Composition" filed on May 14, 2009.

Husmark et al., U.S. Appl. No. 12/514,851, entitled "Hygiene Tissue Comprising a Microbe-Inhibiting Composition" filed on May 14, 2009.

\* cited by examiner

BIOLOGICALLY PURE STRAIN OF *LACTOBACILLUS FERMENTUM*, STRAIN ESS-1

TECHNICAL FIELD

The present invention relates to the field of probiotic bacteria having a beneficial effect on *Candida* yeast infections, i.e. candidiasis, and bacterial infections. The invention also relates to pharmaceutical compositions and products for personal care comprising such bacteria, and the medical use of such bacteria.

BACKGROUND ART

The usual flora in the urogenital region is constituted by a complex ecosystem comprising more than 50 different bacterial species (Hill et al., Scand. J. Urol. Nephrol. 1984(86 (suppl.)):23-29). The normal flora is dominated by bacteria belonging to the genus *Lactobacillus* (LB) which are Gram positive rods adapted to the environment in the vagina of the fertile woman. These bacteria also contribute to the maintenance of the specific milieu and the ecological balance in the vagina. The surrounding pH in the vagina is lower than 4.5. Yeast and enterobacteria are scanty or absent (Redondo-Lopez et al, Rev. Inf. Dis. 1990(12):856-872).

Some LB strains inhibit growth of potentially pathogenic bacteria by various mechanisms. The metabolism of LB results in formation of organic acids, in particular lactic acid and acetic acid, which contribute to the low pH of vaginal fluid, which is unfavorable for many other microbial species. LB may also produce soluble substances which directly inhibit growth of potentially pathogenic bacteria and yeast. They can also produce hydrogen peroxides, which is toxic to bacteria and fungi. These inhibiting characteristics may vary considerably between different LB strains (Hooton et al., JAMA 1991(265):64-69).

Similarly to the urogenital area, the skin is colonized by an array of organisms, which forms its normal flora. The numbers and identity of the organisms vary between different skin sites, with moist and lipid skin areas harbouring more microorganisms per skin area. This, together with the skin's structural barrier, provides the host with an excellent defense against invading microbes. The number of bacteria on the skin varies from a few hundred per $cm^2$ on the arid surfaces of the forearm and back, to tens of thousands per $cm^2$ on the moist areas such as the axilla and groin. This normal flora plays an important role in preventing 'foreign' organisms from colonizing the skin, but it to needs to be kept in check, in order to avoid skin infections.

The gastro intestinal (GI) tract, from mouth to anus, harbors a rich flora of more than 500 different bacterial species, some of which have important health functions. The GI flora consists of about $10^{14}$ bacteria and a low number of commensally yeast. Due to a changed general health state, *Candida* species may overgrow and cause superficial infections. Furthermore, overgrowth of *Candida* species among immunocompromised patients can lead to a systemic infection which is a very serious condition.

Weakness of or imbalance in the natural defense system may allow potentially pathogenic micro-organisms to cause clinical infection, for example in connection with medication, inferior personal care, or shifts in the microflora or mucous membranes. Shifts in the micro-flora can also be found in connection with different pathogenic conditions.

Yeast organisms are always present in humans, but are usually prevented from overgrowth by the indigenous microbial flora. Candidiasis is an infection caused by *Candida* yeast organisms that affects a wide variety of organ systems. Most commonly, the infection is caused by *Candida albicans*, and *C. glabrata*. Less commonly, *C. tropicalis*, *C. parapsilosis*, and *C. kruseii* cause the infection and rarely, other *Candida* species are the causative agent. Candidiasis is often triggered by hormonal changes, such as during pregnancy, menstruation and the use of birth control pills. Other common causes are imbalances in the pH in the vagina, diabetes mellitus, and antibiotic cures, disturbing the delicate microbiological balance of the body. The natural host defense against *Candida* infections include mechanical barriers, non-specific antimicrobial substances (polypeptides, basic proteases), phagocytosis, and specific immune response (T- and B-lymphocytes, delayed-type hypersensitivity.

In immunocompetent persons, any warm, moist part of the body exposed to the environment is susceptible to infection causing vaginitis; vulvar rash; oral thrush; conjunctivitis; endophthalmitis; diaper rash; and infections of the nail, rectum, and other skin folds. In immunocompromised patients, systemic illnesses such as myocarditis, hepatosplenic abscess, pulmonary infection, CNS infection, and chronic disease may occur. Candidiasis may spread from a local infection to cause a systemic infection with serious complications, such as myocarditis, endophthalmitis and hepatosplenic abscess. It is therefore of great importance to find effective cures and preventive treatments for candidiasis, to avoid this serious condition in subjects.

Thrush is the common name for a mouth infection caused by the *Candida albicans* fungus that affects moist surfaces around the lips, inside the cheeks, and on the tongue and palate. Thrush is common in people with diabetes or irritation from dentures. Also people with diseases such as cancer and AIDS, which both suppress the immune system, are often affected by candidiasis.

A *Candida* infection of the mouth can spread to the esophagus, causing esophagitis. This infection is most common in people with AIDS and people receiving chemotherapy for cancer.

*Candida* infection are also common on moist skin parts, such as skin areas covered by diapers, the hands of people who routinely wear rubber gloves, the rim of skin at the base of the fingernail, especially for hands that are exposed to moisture, areas around the groin and in the crease of the buttocks, and the skin folds under large breasts.

Vaginitis is an inflammation of the vaginal mucosa caused by bacteria or fungi. Vaginitis is in itself initially harmless but can lead to premature birth in pregnant women or infertility.

Vaginal candidiasis causes an itching and irritated vagina with whitish, limpy discharge that may resemble cottage cheese. It is often very discomforting for the woman experiencing the symptoms and in addition causes restrictions to normal activities, such as sport exercises and sexual activity.

Vaginal candidiasis is normally treated locally by creams, suppositories, gelatin capsules, vaginal tablets and ointments comprising antifungal agents. Orally administered cures are also available. One problem with antifungal agents is an increased resistance of the fungus to the agent if used repeatedly. In addition, such cures are often inefficient and require a doctor's prescription.

Home remedies, such as application of yoghurt, acidophilus tablets or vinegar douches are also used for treating candidiasis. However, the efficiency of these treatments has been low. Although yoghurt comprises lactobacilli, these are not especially adapted for killing or reducing the growth of fungi. As is understood by the person skilled in the art, such a treatment can only be effective to mitigate the symptoms of minor infections. It has also been suggested that lactic acid producing bacteria can be delivered via absorbent articles, such as diapers, sanitary napkins, panty liners and tampons, as described in e.g. WO97/02846, WO99117813, WO99/45099 and WO00/35502.

There is an increasing interest in finding probiotic microorganisms being able to restore a healthy microbial flora and/or prevent the uncontrolled growth of unwanted microorganisms. Administration of such probiotic bacteria do not have the negative side effects of antifungal agents and preferably are more efficient in the treatment and/or prevention of fungal infections. Previous attempts to find such microorganisms have had various successes though, due to problems such as low attachment and survival of the probiotics in the vagina, limited efficiency in the prevention of fungal growth, low survival during storage of the preparations etc. Other important features of a selected probiotic is ability to grow in the presence of oxygen and survive freeze-drying. Most importantly though, the probiotic bacterium selected must be efficient in the killing and/or prevention of growth of unwanted fungi and/or bacteria. Probiotic lactobacilli have previously been proven efficient in the treatment and prevention of bacterial vaginitis. However, success in the prevention and/or treatment of vaginal candidiasis has been very limited. Therefore, there is still a need for the development of efficient probiotics for the treatment of candidiasis, including vaginal candidiasis, that also may be effective against bacterial infections, such as urinary tract infections.

SUMMARY OF THE INVENTION

The object of the invention is to provide a probiotic bacterium for the treatment and/or prevention of candidiasis and/or bacterial infections, such as urinary tract infections.

The above defined object is in a first aspect of the invention achieved by providing a novel *Lactobacillus fermentum* strain, referred to as Ess-1, which has been deposited as the Sammlung von Mikroorganismen und Zellkulturen GmbH and has been assigned accession number DSM17851.

In another aspect the invention relates to the use of *Lactobacillus fermentum*, strain Ess-1, for the use as a medicament.

In another aspect the invention relates to the use of *Lactobacillus fermentum*, strain Ess-1, for the preparation of a pharmaceutical composition for the prevention and/or treatment of candidiasis.

In another aspect the invention relates to the use of *Lactobacillus fermentum*, strain Ess-1, for the preparation of a pharmaceutical composition for the prevention and/or treatment of bacterial infections, such as urinary tract infection.

In yet another aspects the invention relates to a pharmaceutical composition comprising *Lactobacillus fermentum*, strain Ess-1, optionally together with a pharmaceutically acceptable carrier, excipient and/or diluent.

In a yet further aspect, the invention relates to a sanitary article comprising *Lactobacillus fermentum*, strain Ess-1.

The invention also relates to a method of preparing a pharmaceutical composition for the treatment and/or prevention of candidiasis comprising adding *Lactobacillus fermentum* strain Ess-1, to said pharmaceutical composition.

In addition, the invention relates to a method of preparing an sanitary article for the treatment and/or prevention of candidiasis comprising adding *Lactobacillus fermentum*, strain Ess-1, to a sanitary article.

Since the novel strain of *Lactobacillus fermentum*, strain Ess-1, has been demonstrated to provide excellent inhibition of growth of *Candida* fungi, this novel bacteria strain has shown valuable properties for use in the preparation of a medicament for the treatment and/or prevention of candidiasis. In addition the invention solves the problem of providing products and articles for the delivery of this novel bacterial strain to body areas of interest for such a treatment and/or prevention.

DEFINITIONS

In the present context an antifungal agent is a drug used to treat fungal infections, which drug is not a probioticum as defined below.

Probioticum/probiotics in the present context relates to live microorganisms that confer a health benefit when administered in adequate amounts to a host.

Candidiasis in the present context relates to an infection caused by *Candida* fungi present in or on any body part, such as the skin, urogenital region, mouth, oesophagus or intestines.

Oral supplement in the present context relates to a composition that is orally administered, such as a spray, a tablet, a chewing gum etc.

Biologically pure in the present context relates to a culture of a bacterium which only contains one specific bacterial strain.

The term "sanitary article" refers to products that are placed against the skin of the wearer to absorb and contain body exudates, like urine, faeces and menstrual fluid, and also to products that are used for cleaning and caring of the skin and the urogenital area and that also can be used to deliver probiotic bacteria to these areas. The invention mainly refers to disposable sanitary articles, which means articles that are not intended to be laundered or otherwise restored or reused as a sanitary article after use. Examples of disposable sanitary articles include wet wipes, dry wipes, feminine hygiene products such as sanitary napkins, panty liners, sanitary panties and tampons; feminine inserts; diapers and pant diapers for infants and incontinent adults; incontinence pads; diaper inserts and the like.

The term "absorbent article" refers to products that are placed against the skin of the wearer to absorb and contain body exudates, like urine, faeces and menstrual fluid. Examples of disposable sanitary articles include feminine hygiene products such as sanitary napkins, panty liners, sanitary panties and tampons; feminine inserts; diapers and pant diapers for infants and incontinent adults; incontinence pads; diaper inserts; and the like.

By "hygiene tissue" is meant any device for wiping skin, for instance a washcloth, patch, towelette, napkin, wet wipe, dry wipe and the like.

By "lipid" is in the present context meant substances that are insoluble in water but soluble in an organic solvent.

BRIEF DESCRIPTION OF THE DRAWINGS

FIG. 2 shows the growth inhibition on *C. albicans* in 50 mM ascorbic acid (FIG. 2*a*) and 50 mM propionic acid (FIG. 2*b*), in Ess-1 filtrate and in Ess-1 filtrate with addition of 50 mM ascorbic acid (FIG. 2*a*) and 50 mM propionic acid (FIG. 2*b*). 0 indicates no visual growth, 5 indicates very good growth.

DETAILED DESCRIPTION OF THE INVENTION

The present invention is related to a novel strain of *Lactobacillus fermentum*, hereinafter called Ess-1, deposited according to the Budapest Treaty at Deutsche Sammlung von Mikroorganismen und Zellkulturen GmbH (Mascheroder Weg 1b, D-38124 Braunschweig) and assigned accession number DSM17851 (depositor Essum AB, Box 3160, SE 90304 Umeå, Sweden, deposited on Jan. 6, 2006). The strain has shown unique properties in the treatment/and or prevention of *Candida* infections, i.e. candidiasis, due to its inhibitory properties on growth of *Candida* yeast. Also the strain Ess-1 has shown valuable properties in the treatment and/or prevention of bacterial infections, such as urinary tract infections. In addition, Ess-1 survives long periods of storage which is important for convenience when handling products comprising the bacterium. Also, Ess-1 is not strictly anaerobic but can grow in the presence of oxygen and survives freeze-drying well. The Ess-1 strain of *Lactobacillus fermentum* of the invention is biologically pure.

As demonstrated in Example 1, Ess-1 exhibit a unique inhibition of growth of different strains of *Candida* yeast. In this experiment a large number of *Lactobacili* strains were tested for their growth inhibitory properties of *Candida*. The 23 best strains were chosen for further studies. The growth inhibition of Ess-1 is more than twice than can be demonstrated for the best out of these 23 different *Lactobacillus* strains used for comparison. Also, Ess-1 was demonstrated to inhibit growth of a number of different bacterial strains known to cause urinary tract infection. In addition, Ess-1 was demonstrated to be able to colonize and survive in the vagina when administered to the vagina. Importantly, Ess-1 survives in the vagina also during menstruation. Colonization and survival in vivo after administration to a subject is an important factor for the success of a probioticum to perform its intended tasks. However, lack of, or limited, colonization and survival in vivo often limit the practical usefulness of probiotic lactic acid producing bacteria. In addition, limited survival during storage and handling of products comprising lactic acid producing bacteria often result in the use of ineffective products.

In a first aspect the present invention relates to a novel *Lactobacillus fermentum* strain, denoted strain Ess-1, which has been deposited at Deutsche Sammlung von Mikroorganismen und Zellkulturen GmbH and has been assigned accession number DSM17851.

Due to strain Ess-1's inhibitory properties on growth of *Candida* and bacteria causing urinary tract infections, the present invention also relates to the medical use of this strain. In particular the invention relates to the use of strain Ess-1 for the preparation of a pharmaceutical composition for the prevention and/or treatment of candidiasis preferably of a mammal subject, more preferably a human subject. The invention in another preferred embodiment relates to the use of strain Ess-1 for the preparation of a pharmaceutical composition for the prevention and/or treatment of candidiasis in the urogenital region, such as vaginal candidiasis. In another preferred embodiment, the present invention relates to the use of strain Ess-1 for the preparation of a pharmaceutical composition for prevention and/or treatment of esophagitis. Another preferred embodiment of the present invention relates to the use of strain Ess-1 for the preparation of a pharmaceutical composition for the treatment of thrush.

As the novel Ess-1 strain of the present invention was experimentally (see "Experimental section") shown to inhibit growth of a number of different bacteria causing infection, such as urinary tract infection, another aspect of the invention relates to the use of strain Ess-1 for the preparation of a pharmaceutical composition for the prevention and/or treatment of bacterial infections, such as urinary tract infection.

In one aspect the present invention relates to the use of *Lactobacillus fermentum*, strain Ess-1, which has been deposited at Deutsche Sammlung von Mikroorganismen und Zellkulturen GmbH and has been assigned accession number DSM17851, for the preparation of a pharmaceutical composition for oral administration.

In one preferred embodiment the pharmaceutical composition comprising *Lactobacillus fermentum*, strain Ess-1, also comprises one or more pharmaceutically acceptable carriers, excipients and/or diluents. Generally such agents should be non-toxic to the recipients at the concentrations and dosages used. Examples of such agents are buffers, thickening agents of gel forming agents such as glycerine, polyethylene glycol, antioxidants (e.g. ascorbic acid), polypeptides of low molecular weight (less than about 10 residues), proteins, carbohydrates including glucose, sucrose and dextrins. Examples of carriers include sugars, such as lactose, glucose and sucrose; starches, such as corn starch and potato starch; cellulose and its derivatives such as sodium carboxymethycellulose, ethylcellulose and cellulose acetates; trehalose; powdered traganth, malt; gelatin; talc; stearic acids; magnesium stearate; calcium sulfate; polyols such as propylene glycol, glycerine, sorbitol, mannitol, and polyethylene glycol; agar; alginic acids; pyrogen-free water; isotonic saline; and phosphate buffer solution. In one preferred embodiment of the invention, a carrier providing an anhydrous environment is used as a carrier for the probiotic bacteria. Such an anhydrous environment prolongs the survival of the bacteria during manufacture, transport and storage. One example of such carriers are lipid carriers including petroleum-derived lipids, such as paraffinum liquidum (mineral oils, paraffin oils, and other oils), petrolatum (Vaseline and petroleum jelly), cera microcrystalline, ozokerite, ceresine and paraffins. Alternatively, synthetic lipids, such as dimethicone, cyclomethicone and silicone esters, such as cetearyl methicone can be used. A third alternative is to use animal- or plant-derived lipids, which usually are triglycerides. The animal- and plant-derived lipids are often mixtures of mono-, di- and triglycerides and free fatty acids. The lipids may be purified, hydrogenated, refined, modified and used alone or in different mixtures. Examples of suitable, original animal-derived lipids include beeswax, emu oil, lactic lapida, lanolin, shark liver oil and tallow. Examples suitable of plant-derived original lipids include apricot kernel oil, arachis oil, avocado oil/wax, bayberry wax, black currant seed oil, borage seed oil, brazil nut oil, camelia sinensis oil, candelilla wax, canola oil, carnauba wax, castor oil, cocoa butter, coco-nut oil, corn oil, cotton seed oil, dog rose seed oil, evening primrose seed oil, grape seed oil, illipe butter, jasmine wax, jojoba wax, lavender wax, linseed oil, mango seed oil, olive oil, orange wax, palm oil, palm kernel oil, peanut oil, rice wax, safflower oil, sesame seed oil, shea butter, soybean oil, sunflower seed wax, sweet almond oil, oil of theobroma and wheat germ oil. The use of lipid carriers has the additional advantage of increasing the transfer of bacteria to the user, for example when the pharmaceutical composition is administered via a sanitary product, such as an absorbent product or a hygiene tissue (see e.g. WO 04/060416). Examples of preferred lipids include petrolatum and silicon wax. Wetting agents and lubricants such as sodium lauryl sulfate, and coloring agents, lubricants, tabletting agents, stabilizers and preservatives can also be present. Preferred pharmaceutically acceptable carriers are trehalose or a *lactobacillus* growth factor, e.g. inulin and/or oligofructose, polydextrose, lactitol or resistant starch, in powder or other form. A pharmaceutical composition according to the present invention may in one preferred embodiment also comprise, in addition to *Lactobacillus fermentum* Ess-1 cells, an organic acid and/or a salt thereof, such as acetic acid, propionic acid, lactic acid, ascorbic acid, phenylalanine, citric acid, butyric acid, valeric acid, capronic acid, succinic acid and/or a salt thereof, preferably acetic acid, propionic acid, lactic acid, ascorbic acid, phenylalanine, citric acid or succinic acid and/or a salt thereof, most preferably ascorbic acid, acetic acid, propionic acid, succinic acid and/or a salt thereof. A synergistic effect may be obtained by combining the probiotic Ess-1 with organic acids and/or salts thereof, which organic acid has a pKa value not exceeding 5.5. The organic acids or the corresponding salts should be of such nature that when applying them onto a sanitary article they should not cause any skin irritation to the wearer of the sanitary article, therefore the pKa of the organic acid, when the measurement are performed in water at 25° C., should preferably not be lower than 2. If the pKa values instead are too high, the organic acids or the salts thereof will mainly be in their acid forms. This means that the additive will not be sufficiently dissociated into a hydrogen ion and its deprotonated, anionic form, which is believed to be a prerequisite for said effect with the probiotic bacteria or the extracellular product thereof. Therefore at least one of the pKa values for the organic acid suitable for the present invention should be lower than 5.5, preferably lower than 5. In addition, nutrients for bacterial propagation, such as amino acids, peptides, nucleic acid derivatives, vitamins, salts, fatty acids, glucose, fructose, ribose, maltose and lactose can be added to the pharmaceutical composition, alone or in different combinations.

A pharmaceutical composition according to the present invention is preferably administered in the form of a spray, cream, powder, suppository, liquid for oral administration, capsule, tablet, vaginal insert or oral supplement. Compositions for dermal treatment may e.g. be prepared according to US 2006/0171936.

Other examples of products comprising strain Ess-1 are a powder in a glove, lozenge, chewing gum, mouth wash or mouth spray.

In addition, a pharmaceutical composition according to the present invention may also comprise a substance that reduces odors, such as zeolites, silica, cyclodextrin and activated carbon. Also, substances which have the ability to increase the attachment of lactobacilli and/or substances that decrease the attachment of pathogenic microorganisms may be comprised in a pharmaceutical composition according to the invention.

The pharmaceutical composition according to the present invention can be administered as a single dose, but is preferably administered in multiple doses. The pharmaceutical composition may also preferably be administered in connection with the administration of antifungal agent(s).

In one preferred embodiment the pharmaceutical composition according to the invention comprises dried bacterial cells, such as freeze dried cells, spray dried cells or air dried cells. Such cells have good survival abilities during storage (see the experimental section of a study of survival of freeze dried cells).

The pharmaceutical composition according to the invention comprises preferably $10^4$ to $10^{11}$ colony forming units (cfu), more preferably $10^6$ to $10^{10}$ cfu, even more preferably $10^8$ to $10^{10}$ CFU, of *Lactobacillus fermentum* strain Ess-1 per dose.

The pharmaceutical composition or product according to the invention may, in addition to Ess-1, comprise other bacteria with probiotic properties in order to obtain a broader clinical effect. Preferred such bacteria for the object of the present invention include lactic acid producing bacteria, e.g. from the genera *Lactobacillus, Lactococcus, Pediococcus*, non-pathogenic members of the *Bacillus* genus, all members of the *Bifidobacterium* genus, and *Pseudomonas limbergii*. Preferred members of the *Lactobacillus* genus include *Lactobacillus acidophilus, Lactobacillus bulgaricus, Lactobacillus casei, Lactobacillus cereale, Lactobacillus delbrukeii, Lactobacillus fermentum, Lactobacillus gaserii, Lactobacillus jensenii, Lactobacillus plantarum, Lactobacillus rhamnosus, Lactobacillus salivarius, Lactobacillus thermophilus, Lactobacillus papacasai* sp. *paracasai, Lactobacillus crispatus, Lactobacillus helveticus, Lactobacillus lactis* and the like. More preferably the selected bacterium used is from the species *Lactococcus lactis, Lactobacillus acidophilus, Lactobacillus curvatus* or *Lactobacillus plantarum*. Other preferred examples include non-pathogenic species of *Coccus* species, such as *S. nalivarius, S. oralis* and *S. mitis*. One even more preferred example of such a lactic acid producing bacterium include, but is not limited to, *Lactobacillus plantarum*, strain LB931 (EP 1060240, accession number DSM 11918 with the Deutsche Sammlung von Mikroorganismen).

The pharmaceutical composition according to the invention may be incorporated in a variety of different products. For example, a powder comprising Ess-1 may be provided in different types of protection gloves. Such gloves often provide a humid environment for the hands which may facilitate the growth of fungus resulting in fungal infections of the skin and nails of hands.

The present invention in another aspect relates to a sanitary article comprising *Lactobacillus fermentum* strain Ess-1, which has been deposited at Deutsche Sammlung von Mikroorganismen und Zellkulturen GmbH and has been assigned accession number DSM17851. Such a sanitary article may be an absorbent article such as a feminine hygiene product such as a sanitary napkin, a panty liner, a sanitary panty or tampon; feminine insert; a diaper and pant diaper for infants or incontinent adults; an incontinence pad; or a diaper insert. Also, a sanitary article may be a hygiene tissue such as a washcloth, patch, towelette, napkin, wet wipe or dry wipe. A hygiene tissue suitable for the present invention has previously been described in WO 04/060416. The lactic acid producing bacteria were there "encapsulated" in a lipid in an anhydrous environment in order to protect the bacteria from moisture during storage and to facilitate transfer to the user of the hygiene tissue. Such a hygiene tissue may also optionally comprise one or more cleaning additives such as emollients, emulsifiers, moisturizers, pH-regulating agents, chelating agents, viscosity modifiers, antimicrobial agents, preservatives and fragrances, as disclosed in WO 04/060416. Further details on suitable agents commonly added to skin cleaning products are given in Woodruff's Ingredients and Formulary Handbook, John Woodruff, First ed., 1997, Miller Freeman fJK Ltd. An absorbent product or hygiene tissue according to the invention may also further comprise acids, salts, odour inhibitors, substances that affect the adhesion of probiotics and unwanted microorganisms as discussed above. Such an absorbent product may include a permeable outer sheet which is intended to be in close contact with the skin of the wearer, a preferably liquid-impermeable backing sheet which is intended to lie distal from the wearer in use, and an absorbent structure arranged between the outer sheet and the backing sheet. In some cases, an additional sheet in the form of e.g. wadding or like material, may be placed between the outer sheet and the absorbent structure. The backing sheet is preferably breathable. The probiotic bacteria may be arranged in different parts of the absorbent article, for instance in the outer sheet, in the absorbent structure, between two of the layers of the absorbent article, in a loose insert product in the absorbent product, or in some other way. An absorbent product according to the present invention may also preferably comprise a superabsorbent polymer (SAP).

A sanitary article according to the invention may in addition to *Lactobacillus fermentum* Ess-1 cells further comprise an organic acid and/or a salt thereof, such as acetic acid, propionic acid, lactic acid, ascorbic acid, phenylalanine, citric acid, butyric acid, valeric acid, capronic acid, succinic acid and/or a salt thereof, preferably acetic acid, propionic acid, lactic acid, ascorbic acid, phenylalanine, citric acid or succinic acid and/or a salt thereof, most preferably ascorbic acid, acetic acid, propionic acid, succinic acid and/or a salt thereof, which acid has a pKa value not exceeding 5.5. A synergistic effect may be obtained by combining the probiotic Ess-1 cells with organic acids and/or salts thereof.

A sanitary article according to the invention preferably comprises $10^4$ to $10^{11}$ colony forming units (cfu), more preferably $10^6$ to $10^{10}$ cfu, even more preferably $10^8$ to $10^{10}$ CFU, of *Lactobacillus fermentum* strain Ess-1 per sanitary article.

The probiotic bacteria of the present invention can be directly applied to a sanitary article according to the invention or provided in a pharmaceutical composition as disclosed herein applied to the product. In one preferred embodiment the bacteria are dried bacteria, as disclosed above, are applied directly to the sanitary article, alone or in a pharmaceutical composition according to the above. In another preferred embodiment the bacteria can be applied to the sanitary article first, e.g. in a suspension comprising the bacteria, whereafter the sanitary product is dried, thereby providing a product with bacteria dried in thereon, optionally in combination with additional pharmaceutical agents as disclosed above. In another preferred embodiment, the dried bacterial powder are provided in a lipid added to the sanitary article. In order to reduce exposure of the bacteria to moisture during manufacture, transport and storage of articles comprising the probiotic Ess-1, in one preferred embodiment the sanitary article is packed in a water impermeable package.

In another aspect the invention relates to the use of *Lactobacillus fermentum* strain Ess-1, which has been deposited at Deutsche Sammlung von Mikroorganismen und Zellkulturen GmbH and has been assigned accession number DSM17851, for producing a sanitary article such as a wet wipe, dry wipe, a feminine hygiene product such as a sanitary napkin, panty liner, sanitary panty and tampon; a feminine insert; a diaper or pant diaper for infants or incontinent adults; an incontinence pad; or a diaper insert. The sanitary article is preferably an absorbent article such as a feminine hygiene product such as a sanitary napkin, a panty liner, a sanitary panty or tampon; a feminine insert; a diaper and pant diaper for infants or incontinent adults; an incontinence pad; or a diaper insert. The sanitary article may also preferably be a hygiene tissue such as a washcloth, patch, towelette, napkin, wet wipe or dry wipe.

The invention also relates to the use of *Lactobacillus fermentum* strain Ess-1, which has been deposited at Deutsche Sammlung von Mikroorganismen und Zellkulturen GmbH and has been assigned accession number DSM17851, for producing a pharmaceutical composition such as a suspension, spray, cream, powder, suppository, capsule, tablet, oral supplement or a vaginal insert etc., according to the above.

Pharmaceutical compositions and products comprising *L. fermentum* strain Ess-1 comprise a therapeutically effective amount of this bacterial strain.

The present invention also relates to a method for treating and/or preventing a candidiasis comprising the administration of a therapeutically effective amount of *Lactobacillus fermentum* strain Ess-1, which has been deposited at Deutsche Sammlung von Mikroorganismen und Zellkulturen GmbH and has been assigned accession number DSM17851, to a subject in need thereof. The invention also relates to a method for treating and/or preventing bacterial infections, such as urinary tract infection, comprising the administration of a therapeutically effective amount of *Lactobacillus fermentum* strain Ess-1, which has been deposited at Deutsche Sammlung von Mikroorganismen und Zellkulturen GmbH and has been assigned accession number DSM17851, to a subject in need thereof. In such methods, strain Ess-1 is administered to the subject via any of the pharmaceutical compositions or products, which have been disclosed above. For administration via a sanitary article, such as an absorbent product, it is important that the absorbent product is placed in close contact with the skin of said subject.

One important objective of the present invention is the oral administration of Ess-1. One aspect of the invention therefore relates to a pharmaceutical composition for oral administration. This oral administration in a first aspect leads to the suppression of growth of fungi and/or bacteria in the gastrointestinal tract and an improvement of the balance in the microbial flora. However, fungi and bacteria present in the gastrointestinal tract may also be transferred to the urogenital area via the anus. Suppression of fungal and/or bacterial growth in the gastrointestinal tract may therefore have a beneficial effect both on the gastrointestinal tract itself, but also on the urogenital area due to a reduced spreading of pathogenic fungi and/or bacteria to this region. A systemic effect may also be achieved, such as triggering of immune response substances. Oral administration can e.g. be provided via Ess-1 being comprised in capsules, tablets, troches, lozenges, pastilles, liquid suspensions, dry oral suspensions, liquid oral suspensions, chewing gums, mouth washes, pastilles, mouth sprays, vials etc. Oral administration may also be achieved via food products, such as yoghurt, milk, fresh cheese, ice cream, products made of fermented milk, products made of fermented cereals, milk powder etc, and childrens' products, such as gruel.

In another aspect the present invention relates to products for the topical and/or oral administration of strain Ess-1 to an animal for improving animal health, e.g. in a pharmaceutical composition according to the above or in feedstuff or a feed supplement for an animal. Also Ess-1 may be used to improve the quality of the animal feedstuff, such ensilage, in itself by inhibiting growth of fungi and bacteria therein.

The present invention also relates to a method of preparing a pharmaceutical composition for the treatment and/or prevention of candidiasis comprising adding *Lactobacillus fermentum* strain Ess-1, which has been deposited at Deutsche Sammlung von Mikroorganismen und Zellkulturen GmbH and has been assigned accession number DSM17851, to said pharmaceutical composition. The present invention also relates to a method of preparing a pharmaceutical composition for the treatment and/or prevention of bacterial infections, such as urinary tract infections, comprising adding *Lactobacillus fermentum* strain Ess-1, which has been deposited at Deutsche Sammlung von Mikroorganismen und Zellkulturen GmbH and has been assigned accession number DSM17851, to said pharmaceutical composition.

Also, the present invention relates to a method of preparing a sanitary article, such as an absorbent product or a hygiene tissue, for the treatment and/or prevention of candidiasis comprising adding *Lactobacillus fermentum* strain Ess-1, which has been deposited at Deutsche Sammlung von Mikroorganismen und Zellkulturen GmbH and has been assigned accession number DSM17851, to said sanitary article. Also, the present invention relates to a method of preparing a sanitary article, such as an absorbent product or a hygiene tissue, for the treatment and/or prevention of bacterial infections, such as urinary tract infections, comprising adding *Lactobacillus fermentum* strain Ess-1, which has been deposited at Deutsche Sammlung von Mikroorganismen und Zellkulturen GmbH and has been assigned accession number DSM17851, to said sanitary article.

The invention will now be described in more detail in the following experimental section. The examples are however only illustrative and not intended to limit the scope of the present invention.

EXPERIMENTAL SECTION

Example 1

Isolation and Typing of Ess-1

Aim

The initial purpose of this study is to isolate and type a *Lactobacillus* strain that inhibit the growth of *Candida albicans* and *Candida glabrata* to a large extent compared to other *Lactobacillus* strains.

Method

Yeast Strains

Clinical isolates of *Candida albicans* and *Candida glabrata* were used as test strains. These were isolated from the vagina of women with vaginal candidiasis and from healthy females.

Screening I.

About 140 *Lactobacillus* strains, originating from human skin, throat, teeth, baby faeces, vegetables and seeds were cultured in MRS broth and stamped onto MRS agar plates. The agar plates were incubated under anaerobic conditions at 37° C. Additionally, SAB (Sabouraud) agar (LAB M, Bury, UK) was poured onto the MRS agar and was allowed to congeal. *C. albicans* culture was seeded onto the agar and the plates were incubated aerobically at 37° C. A visual evaluation of the inhibition was done. Strains inhibiting *C. albicans* equally or to a greater extent than the reference strain *Lactobacillus plantarum* LB931 were selected for further screening (screening II).

Screening II.

Suspensions of lactobacilli grown in dMRSs broth (MRS broth without addition of sodium acetate) were centrifuged and sterile filtered. The filtrate is henceforth called *Lactobacillus* Cell-free Filtrate, LCF. A specified volume was transferred to wells of a micro titre plate and was let to air dry and thereafter resuspended in sterile distilled water to a concentration three times higher and transferred to 96-wells micro titre plates. *Candida* was added to all vials (three isolates of *C. albicans* and *C. glabrata*, respectively, were used). The inhibition was evaluated by visual observation of turbidity and graduated by two persons using a template on a scale from five to zero. The wells containing strong growth of *Candida* sp. in pure dMRSs-broth were graduated as five, while wells with no visual growth were graduated as zero.

API Typing and Genetic Typing

Identification to the species level was done using the API 50 CHL system (bioMérieux, France), following the manufacturer's instructions. Data from the fermentation tests were analysed using API Lab Plus software. Genetic typing was done by DSMZ (Deutsche Sammlung von Microorganismen und Zellkulturen GmbH) by partial sequence analysis of the 16S rRNA.

Results

Figure 1:
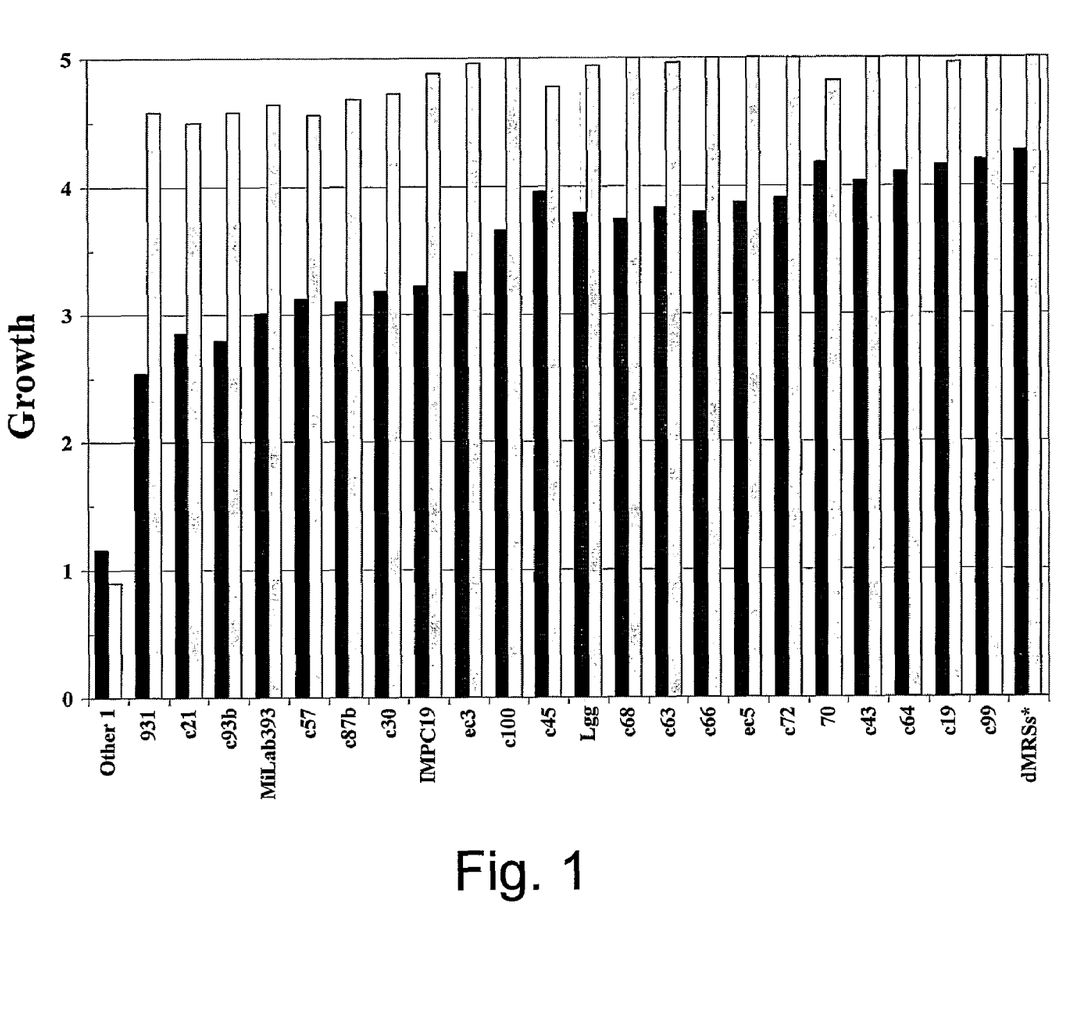
FIG. 1 shows the mean inhibition of growth on three strains each of *C. albicans* and *C. glabrata*. ■=*C. albicans*, □=*C. glabrata*. *dMRSs pH adjusted to the lowest registered pH of all filtrates (pH 3.7). 0 indicates no visual growth, 5 indicates very good growth.

All strains were evaluated according to the growth inhibition capacity against *C. albicans* in screening I. 23 *Lactobacillus* strains with results comparable or exceeding the one for LB931 were selected for screening II. Out of those 23 *Lactobacillus* strains, three were reference strains and a majority of the strains had been isolated from the oral tract. FIG. 1 illustrates the growth inhibition for each *Lactobacillus* strain, where each bar represents the mean growth of three *C. albicans* strains and three *C. glabrata* strains respectively.

"Other 1" proved to have a comprehensive capacity to inhibit growth of *Candida*. No one of the tested *Lactobacillus* strains was similar to the activity of Other 1 regarding the effect on both *C. albicans* and *C. glabrata*. Other 1 was designated Ess-1 and its carbohydrate fermentation pattern and the genetic typing showed that it belongs to the *Lactobacillus fermentum* species.

Characterization of Ess-1

16S rDNA from strain Ess-1 (DSM 17851) was analysed by DSMZ (Deutsche Sammlung von Mikroorganismen und Zellkulturen GmbH) by direct sequencing of about 450 nucleotides of PCR-amplified 16S rDNA. Genomic DNA extraction, PCR mediated amplification of the 16S rDNA and purification of the PCR product was carried our as previously described (Rainey, F. A. et al. Int. J. Sys. Bacteriol. 1996(46): 1088-1092). Purified PCR products were sequenced using the CEQ™DTCS-Quickstart Kit (Beckamn Coulter) following the manufacturers instructions. Sequence reaction products were electrophoresed using the CEQ™8000 Genetic Analysis System.

The resulting sequence data was put into the alignment editor ae2 (Maidak, B. L. et al. Nucl. Acids Res. 1999(27): 171-173), aligned manually and compared with representative 16S rRNA gene sequences of organism belonging to the *Firmicutes* (Maidak, B. L. et al.). For comparison 16S rRNA sequences were obtained from the EMBL data base or RDP (Maidak, B. L. et al.).

As a result of this analysis the following table 1 lists those organisms, whose 16S rRNA gene sequences show the highest similarity values compared to the 16S rDNA sequence of Ess-1.

TABLE 1

| Strain | % 16S rRNA gene sequence similarity to Ess-1 |
|---|---|
| *Lactobacillus fermentum* ATCC 14931 | 99.3 |
| *Lactobacillus fermentum* KRM | 99.0 |
| *Lactobacillus malefermentans* DSM 5705 | 85.5 |
| *Lactobacillus rossiae* ATCC BAA-822 | 88.9 |
| *Lactobacillus suebicus* DSM 5007 | 86.9 |
| *Lactobacillus vaccinostercus* DSM 20634 | 87.2 |

The partial 16S rDNA gene sequence of strain Ess-1 shows highest similarity to *Lactobacillus fermentum*. Consequently strain Ess-1 may represent a strain of *Lactobacillus fermentum*, but may as well represent a new species within the genus *Lactobacillus*.

Example 2

Heat Treatment

Aim

The aim of this experiment is to study the heat resistance for the *Candida* growth inhibiting substances produced by strain Ess-1.

Method

LCF was heat treated for 20 minutes at 90° C. *C. albicans* and *C. glabrata* were added to a final concentration of approximately $5 \times 10^4$ CFU ml$^{-1}$. The plates were incubated for 20 hours at 37° C. and the candida growth in the vials was visually evaluated and graduated from five to zero. Här nämns plates och vials I samma mening.

Results

The heat treated filtrate of strain Ess-1 was as successful in inhibiting growth of yeast as the non-treated filtrate used as a comparison. Therefore, heat treatment of the filtrate did not destroy the active substance of this bacterium.

Example 3

Inhibition of *C. albicans* with LCF with Addition of Salts and Acids

Aim

The purpose of this study is to determine whether salts and acids affects growth of *Candida* and if an improved growth inhibition can be achieved when they are added to the LCF of strain Ess-1.

Method—Salts

Aliquots of LCF were pH adjusted to the pKa-value for each salt and air dried until they were completely dry and thereafter resuspended in 0.3% sodium acetate and sodium propionate. *C. albicans* was added to a final concentration of approximately $5 \times 10^4$ CFU ml$^{-1}$. The fractions were incubated for 20 hours at 37° C. The inhibition was evaluated by visual observation of turbidity and graduated by two persons using a template on a scale from five to zero. The wells containing strong growth of *Candida* sp. in pure dMRSs-broth were graduated as five, while wells with no visual growth were graduated as zero.

Methods—Acids

Succinic acid, acetic acid, propionic acid and ascorbic acid were added to a final concentration of 50 mM to tubes containing LCF. The filtrate was pH adjusted to the pKa-value for the respective acid. *C. albicans* and *C. glabrata* were added to a final concentration of approximately $5 \times 10^4$ CFU ml$^{-1}$. The plates were incubated for 20 hours at 37° C. and the candida growth in the wells was visually evaluated and graduated from five to zero.

Results

Figure 2A:
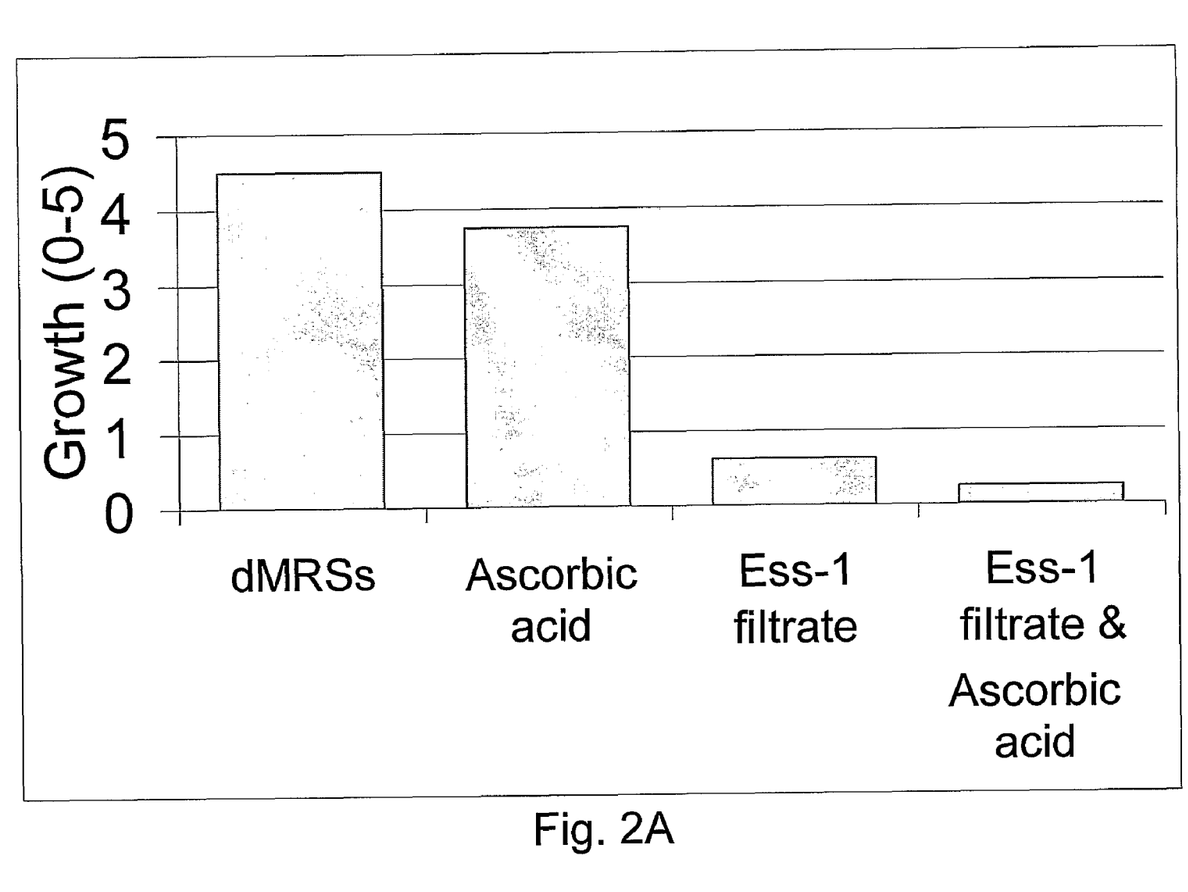
Figure 2B:
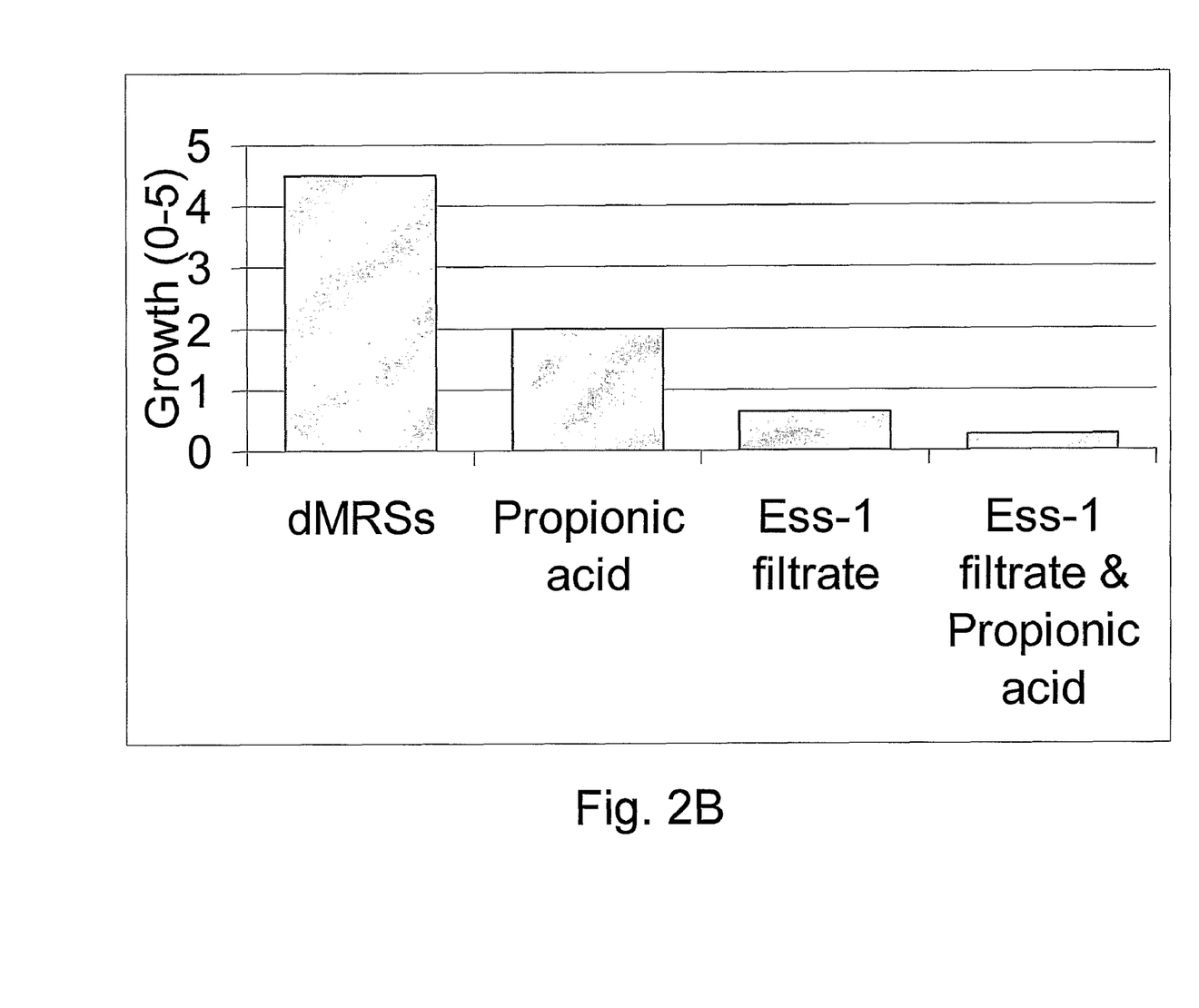

Different acids and acid salts proved to have an effect on the growth of *C. albicans*. Initial results showed that a concentration of 50 mM in the filtrates was the lowest concentration required to see an effect of some acids and 0.1-0.3% to see an effect of salt additives. Sodium propionate and propionic acid had the most extended effect on *C. albicans*. As illustrated in FIGS. 2*a* and *b*, an addition of the growth inhibiting effect was achieved when ascorbic acid (50 mM, pKa and pH: 4.2) or propionic acid (50 mM, pKa and pH: 4.87) was added to the Ess-1 LCF. This demonstrates that a synergistic effect may be obtained by combining the Ess-1 LCF with organic acids and/or salts thereof. Therefore a combination of Ess-1 cells with organic acids and/or salts thereof is predicted to result in a similar synergistic effect.

Example 4

Acid Analysis

Aim

The aim of this study is to investigate whether strain Ess-1 produces acids, which are not produced or produced at a lower level, by other *Lactobacillus* strains, and which could explain the strong growth inhibitory capacity of this bacterial strain on yeast.

Method

Ess-1 and other *Lactobacillus* strains were cultured in 45 ml dMRSs broth (MRS broth without addition of sodium acetate) for 18 h, centrifuged at 10° C., 3000 rpm for 15 minutes, The supernatant was sterile filtered (0.22 ☐m, Millex, Billerica, Mass., USA) and frozen at −55° C. until sent to Steins Laboratorium A7S (Löddeköping, Sweden) for analysis using liquid chromatography.

Results

Figure 3:
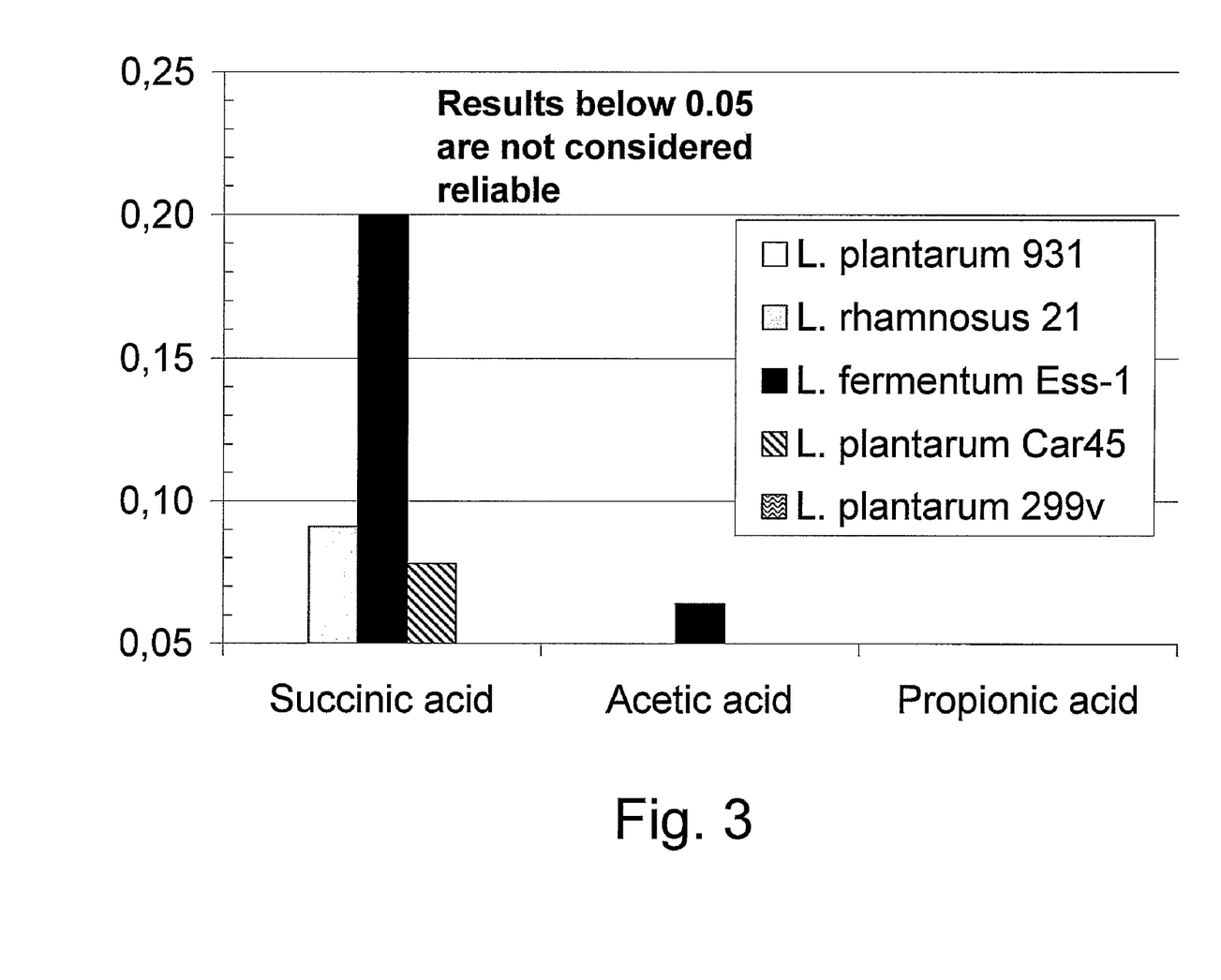
FIG. 3 shows production of succinic acid, acetic acid and propionic acid in five different *Lactobacillus* strains, including Ess-1. The strains were grown in MRS broth and the acid production was registered in the broth after the supernatant had been sterile filtered.

As can be seen in FIG. 3, strain Ess-1 produces more succinic acid and more acetic acid than the other tested bacterial strains, which could be one reason for the excellent inhibitory capacity of this strain on yeast growth.

Example 5

Survival of Ess-1 Through Freeze-Drying and During Storage

Aim

The purpose of this experiment is to determine whether Ess-1 survives freeze-drying and remains viable after storage thereafter.

Method

Ess-1 was grown in MRS, concentrated ten times in a 20% trehalose suspension. The suspension was frozen at −55° C. in a plastic jar. After 24 h the jar was put into a freeze drying machine (Hetosicc, Heto Birkerød, Denmark) and processed for 48 h. The end product was pulverized and placed in an air-tight container for storage. To increase the stress the container was placed at 37° C. Samples were taken at week 0, 2, 5 and 11. Viable bacteria were counted by suspending the powder in sodium chloride solution and see in onto agar plates.

Results

Strain Ess-1 survived freeze-drying well and was stable for 11 weeks with only one log decrease in survival during this time period. After 17 weeks storage the survival was down by 4.5 log. This indicates a very good survival of the bacterium, as normally storage takes place at room temperature or in a fridge, at which temperatures the decrease in survival is even slower.

Example 6

Survival of Strain Ess-1 after Administration to the Vagina of Capsules Comprising Freeze-Dried Bacteria Aim:

To study the survival and colonization of Ess-1 after administration to the vagina.

Method

Ess-1 was grown in MRS, concentrated ten times in a 20% trehalose suspension and freeze-dried as described above. After pulverization of the material the powder was filled into gelatine capsules (size 2, Apoteket AB, Gothenburg, Sweden) to a concentration of approximately $1 \times 10^9$ CFU per capsule. Four voluntary subjects participated in the study by using one capsule per week for one menstrual period, starting the administration the days prior to menses. The subjects took vaginal samples by themselves once a week prior to capsule administration by rotating a sterile cotton pin 5 times 3 cm inside the vagina. The samples were cultured on agar plates and vancomycin resistant lactobacilli morphologically similar to Ess-1, and therefore considered to be Ess-1, were counted.

Results

No women had strong growth of vancomycin resistant lactobacilli at study start. All women were colonized with Ess-1 at the second sample taken the days following menses. Ess-1 was further found throughout the study in some women and in specific samples in others. Thus, vaginal capsules can be used to colonize the vagina throughout the menstrual cycle. The data are presented in Table 2.

TABLE 2

Amount of Ess-1 found in vaginal samples in women participating in the study. Four women were included in the study and no one was colonized with vancomycin resistant *Lactobacillus* strains at study start (Before).

| | Before start of study | Sample 2 | Sample 3 | Sample 4 | Sample 5 | Sample 6 |
|---|---|---|---|---|---|---|
| Woman 1 | 0 | 6.22 | 6.52 | 4.95 | 5.43 | 2.00 |
| Woman 2 | 0 | 4.70 | 0.00 | — | 4.54 | 4.28 |
| Woman 3 | 0 | 1.30 | — | 4.22 | 3.85 | — |
| Woman 4 | 0 | 2.41 | 0.00 | — | — | — |

Data is presented as $Log_{10}$ CFU $ml^{-1}$.
Samples marked "—" are missing.

Example 7

Inhibition of Bacteria Causing Infections such as Urinary Tract Infections

Aim

The purpose of the study was to explore whether Ess-1 produces substances that inhibit growth of bacteria causing infections, such as urinary tract infections.

Method

A modified agar-overlay method was used. Ess-1 was grown in MRS broth for 20 h. 1 ml of bacterial culture was mixed with 2 ml 7.5M sodium acetate solution and 22 ml MRS agar at 50° C. and flooded into a petri dish and let to congeal. The plate was anaerobically incubated at 37° C. for 20 h. An additional layer of 24 ml M17 agar mixed with 0.75 ml 6.5 M potassium dihydrogen phosphate solution was flooded on top of the MRS layer and let to congeal. A Steer's steal pin replicator was dipped into wells of a Bertrani tray containing over night cultures of the pathogens and stamped onto the top agar layer. The plates were left to dry for 30 minutes and incubated at 37° C. for 24 h before reading. Sterile MRS broth was used as control. pH was registered on the top agar layer after incubation and the growth was categorized to "growth" or "no growth". The pathogenic strains (a total of 23 strains) were isolated from women with urinary tract infections; they included *E. coli* (4), *Klebsiella* sp. (4), *E. faecalis* (3), *Enterobacter* (4), Group B *Streptococcus* (3), *S. aureus* (2), *S. saprophyticus* (1) and *P. mirabilis* (2).

Results

Ess-1 inhibited growth of all pathogens and all pathogens grew well on the control plate. The pH was 6.0 on the top agar layer and would thus not impact growth in any way.

The invention claimed is:

1. A biologically pure strain of *Lactobacillus fermentum*, strain Ess-1, which has been deposited at Deutsche Sammlung von Mikroorganismen und Zellkulturen GmbH and has been assigned accession number DSM17851.

2. A pharmaceutical composition comprising $10^4$ to $10^{11}$ colony forming units (cfu) of the biologically pure strain of *Lactobacillus fermentum*, strain Ess-1, which has been deposited at Deutsche Sammlung von Mikroorganismen und Zellkulturen GmbH and has been assigned accession number DSM17851, optionally together with a pharmaceutically acceptable carrier, excipient and/or diluent.

3. The pharmaceutical composition according to claim 2, wherein said pharmaceutically acceptable carrier is trehalose or a lactobacillus growth factor.

4. The pharmaceutical composition according to claim 2, wherein the biologically pure strain of *Lactobacillus fermentum* strain Ess-1 cells are dried.

5. The pharmaceutical composition according to claim 2, further comprising other probiotic bacteria.

6. The pharmaceutical composition according to claim 5, wherein the other probiotic bacteria comprise lactic acid producing bacteria.

7. The pharmaceutical composition according to claim 2, which is a suspension, spray, cream, powder, suppository, capsule, oral supplement or a vaginal insert.

8. The pharmaceutical composition according to claim 2 which is for oral administration.

9. A sanitary article comprising $10^4$ to $10^{11}$ colony forming units (cfu) of the biologically pure strain of *Lactobacillus fermentum* strain Ess-1, which has been deposited at Deutsche Sammlung von Mikroorganismen und Zellkulturen GmbH and has been assigned accession number DSM17851.

10. The sanitary article according to claim 9, further comprising an organic acid and/or a salt thereof.

11. The sanitary article according to claim 9, further comprising other probiotic bacteria, wherein the other probiotic bacteria comprise lactic acid producing bacteria.

12. The sanitary article according to claim 9, which sanitary article is an absorbent article.

13. The sanitary article according to claim 9, which sanitary article is a hygiene tissue.

14. The pharmaceutical composition according to claim 2, wherein the pharmaceutical acceptable carrier is in powder form.

15. The pharmaceutical composition according to claim 1, comprising $10^8$ to $10^{10}$ CFU of the biologically pure strain of *Lactobacillus fermentum* strain Ess-1.

16. The pharmaceutical composition according to claim 6, wherein the lactic acid producing bacteria comprise *Lactobacillus plantarum* LB931, which has been deposited at Deutsche Sammlung von Mikroorganismen und Zellkulturen GmbH and has been assigned accession number DSM11918.

17. The sanitary article according to claim 9, further comprising an acid and/or a salt thereof, wherein the acid is selected from the group consisting of acetic acid, propionic acid, lactic acid, ascorbic acid, phenylalanine, citric acid, butyric acid, valeric acid, capronic acid and succinic acid.

18. The sanitary article according to claim 11, wherein the lactic acid producing bacteria comprise *Lactobacillus plantarum* LB931, which has been deposited at Deutsche Sammlung von Mikroorganismen und Zellkulturen GmbH and has been assigned accession number DSM11918.

19. The sanitary article according to claim 9, comprising $10^8$ to $10^{10}$ CFU of the biologically pure strain of *Lactobacillus fermentum* strain Ess-1 per product.

20. The sanitary article according to claim 12, wherein the absorbent article is:

a feminine hygiene product selected from the group consisting of a sanitary napkin, a panty liner, a sanitary panty, and a tampon;

a feminine insert; a diaper and pant diaper for infants or incontinent adults;

an incontinence pad; or a diaper insert.

21. The sanitary article according to claim 13, wherein the hygiene tissue is selected from the group consisting of a washcloth, patch, towelette, napkin, wet wipe and dry wipe.

* * * * *